United States Patent [19]
Ginsberg et al.

[11] Patent Number: 6,063,907
[45] Date of Patent: May 16, 2000

[54] IN VITRO METHODS FOR DETERMINING IN VIVO THROMBOTIC EVENTS

[75] Inventors: Mark H. Ginsberg, San Diego, Calif.; Andrew L. Frelinger, III, North Reading, Mass.; Edward F. Plow, San Diego, Calif.

[73] Assignee: The Scripps Research Institute, La Jolla, Calif.

[21] Appl. No.: 09/021,290

[22] Filed: Feb. 10, 1998

Related U.S. Application Data

[62] Division of application No. 08/187,829, Jan. 26, 1994, Pat. No. 5,763,580, and a continuation of application No. 07/693,388, Apr. 30, 1991, abandoned.

[51] Int. Cl.⁷ .............................. C07K 14/435; C07K 7/00
[52] U.S. Cl. .................... 530/387.9; 530/350; 530/300; 530/326; 530/327; 530/328; 530/329; 530/388.1; 530/388.25; 530/389.3
[58] Field of Search .............................. 530/387.9, 388.1, 530/388.25, 389.3, 350, 300, 326, 327, 328, 329

[56] References Cited

U.S. PATENT DOCUMENTS

| | | | |
|---|---|---|---|
| 5,114,842 | 5/1992 | Plow et al. ............................. | 530/326 |
| 5,498,499 | 3/1996 | Flow et al. ............................. | 435/7.21 |
| 5,763,580 | 6/1998 | Ginsberg et al. ....................... | 530/350 |

OTHER PUBLICATIONS

Loftus et al., "Molecular cloning and chemical synthesis of a region of a platelet glycoprotein IIb involved in adhesive function," Proceedings of the National Academy of Sciences USA, 84:7114–7118, Oct. 1987.

Shadle et al., "Platelet–Collagen Adhesion: Inhibition by a Monoclonal Antibody That Binds Glycoprotein IIb," The Journal of Cell Biology, 99:20566–2060, Dec. 1984.

Shattil et al., "Changes in the Platelet Membrane Glycoprotein IIb–IIIa Complex during Platelet Activation," The Journal of Biological Chemistry, 260:11107–11114, Sep. 1985.

*Primary Examiner*—James C. Housel
*Assistant Examiner*—Bao-Thuy L. Nguyen
*Attorney, Agent, or Firm*—Thomas Fitting; Emily Holmes

[57] ABSTRACT

Antibodies for detecting the presence of C-terminal hGPIIb fragment of the platelet receptor GPIIb-IIIa in a body fluid sample are disclosed.

2 Claims, 2 Drawing Sheets

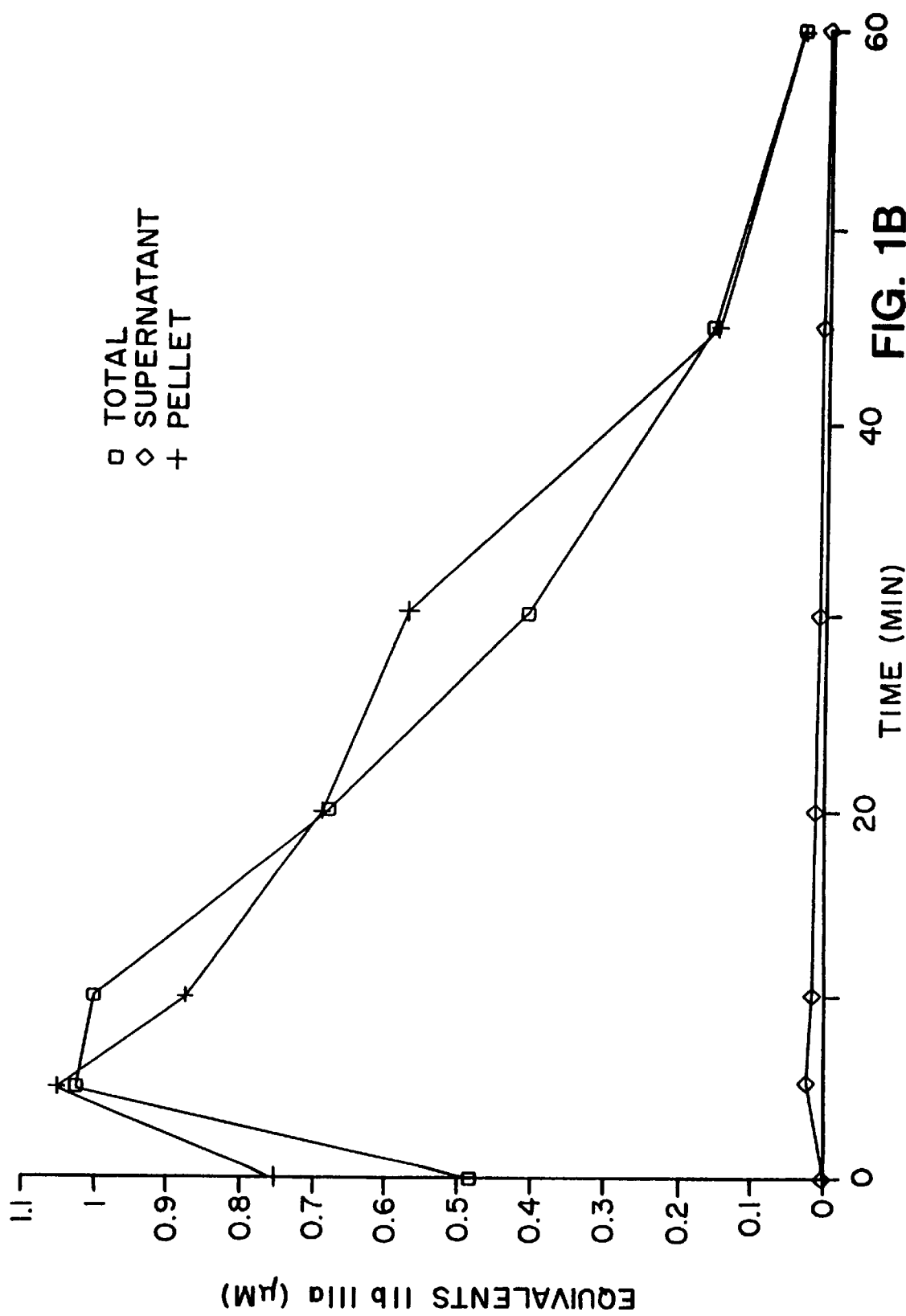

IN VITRO METHODS FOR DETERMINING IN VIVO THROMBOTIC EVENTS

This application is a Divisional of U.S. patent application Ser. No. 08/187,829, filed Jan. 26, 1994 (now U.S. Pat. No. 5,763,580) and a Continuation of U.S. patent application Ser. No. 693,388, filed Apr. 30, 1991 (now abandoned).

This invention was made with government support under contract No. GM37696 by the National Institutes of Health. The government has certain rights in the invention.

TECHNICAL FIELD

The present invention relates to a fragment of the C-terminal region of GPIIb heavy chain (hGPIIb) that is produced in vivo by indigenous protease cleavage of the GPIIb-IIIa platelet glycoprotein receptor, and to in vitro detection of the fragment in body fluids of individuals undergoing thrombotic events. The present invention also relates to polypeptide analogs of the hGPIIb C-terminal fragment, and antibodies that immunoreact with the C-terminal fragment and to diagnostic methods for detecting thrombi and clotting disorders.

BACKGROUND

Thrombosis involves cell adhesion of platelets. Platelet cell adhesion generally involves recognition of specific adhesive proteins by the platelet cell surface receptor GPIIb-IIIa.

GPIIb-IIIa is a noncovalent, $Ca^{++}$ dependent, heterodimer complex comprised of noncovalently associated alpha and beta subunits. Jennings et al., *J. Biol. Chem.*, 257:10458–10466 (1982). The alpha subunit, GPIIb consists of a heavy chain (hGPIIb) having a relative molecular weight of about 120 kilodaltons (KDa), and a light chain (lGPIIb) of about 20 KDa that are linked together by disulfide bonds. The beta subunit, GPIIIa is a single chain polypeptide of about 100 KDa. Phillips et al., *J. Biol. Chem.*, 252:2121–2126 (1977).

GPIIb-IIIa contributes to platelet function through interactions with RGD-containing proteins such as fibrinogen [Bennett et al., *Proc. Natl. Acad. Sci. USA*, 80:2417–2421 (1983)], fibronectin [Ginsberg et al., *J. Clin. Invest.*, 71:619–624 (1983)], and von Willebrand factor [Ruggeri et al., *Proc. Natl. Acad. Sci. USA*, 79:6038–6041 (1982)], and therefore is a component of the common platelet adhesive protein receptor [Pytela et al., *Science*, 231:1559–1562 (1986) and Plow et al., *J. Biol. Chem.*, 259:5388–5391 (1984)].

The sites on GPIIb-IIIa that are required to function as an adhesion receptor are not well characterized. Several observations suggest that a functionally significant site on GPIIb-IIIa is near the epitope defined by the monoclonal antibody PMI-1. This antibody binds to the heavy chain of GPIIb [Shadle et al., *J. Cell. Biol.*, 99:2056–2060 (1984)] and defines a region of GPIIb that is associated with several distinct functional activities. First, PMI-1 inhibits adhesion of washed platelets to collagen. Shadle et al., *J. Cell. Biol.*, 99:2056–2060 (1984). Second, the surface orientation of this region is regulated by divalent cations because millimolar (mM) concentrations of calcium or magnesium suppress expression of the PMI-1 epitope. Ginsberg et al., *J. Clin. Invest.*, 78:1103–1111 (1986). Third, abnormal divalent cation regulation of the conformation of this site is associated with a functional thrombasthenic state. Ginsberg et al., *J. Clin. Invest.*, 78:1103–1111 (1986). Fourth, stimulation of platelets with up to 100 micromolar adenosine diphosphate (ADP) or epinephrine, 1 unit per milliliter thrombin, or 50 micrograms per milliliter calf skin collagen does not substantially increase the binding of PMI-1 antibodies to platelets.

Platelet activation has been reported to produce the appearance of antigenic sites on the platelet surface that are not present in the non-activated platelet, and at least one of such induced sites has been localized to the GPIIb-IIIa receptor complex. Shattil et al, *J. Biol. Chem.* 260:11107–11114 (1985); Coller, B. S., *J. Cell Biol.*, 103:451–456 (1986).

Numerous assays based on the release of fragments of blood coagulation enzymes or platelet activation have been developed in attempts to identify thrombotic and pre-thrombotic states. From the platelet perspective, initial efforts were focused on release of platelet specific antigens. Ginsberg, et al., In *Immunologic Analysis: Recent Progress in Diagnostic Labor. Immunol.*, Nakamura et al., Eds. Masson Publishing, USA Inc., 199–209 (1982). Recent studies have focused on the use of monoclonal antibodies selective for activated platelets. Frelinger et al., *J. Biol. Chem.*, 263:12397–12402 (1988); Aiken et al., *Sem. Thromb. Hemost.*, 13:307–316 (1987); Berman et al., *J. Clin. Invest.*, 78:130–137 (1986); Hsu-Lin et al., *J. Biol. Chem.*, 259:9121–9126 (1984); George et al., *J. Clin. Invest.*, 78:340–348 (1986); Shattil et al., *Blood*, 73:150–158 (1989); Shattil et al., *J. Biol. Chem.*, 260:11107–11114 (1985); Adelman et al., *Blood*, 70:1362–1366 (1987).

Each of the above methods has been plagued by unintentional in vitro activation because it is difficult to obtain blood samples in a manner such that the platelet activation events are not triggered during venipuncture, sample handling or the like. This difficulty has severely limited the clinical utility of such assays. It would be desirable, therefore, to develop a method to detect the occurrence of thrombotic events without relying on platelet activation events. The utility of determining the elevation in a plasma glycocalicin, as a potential assay for in vivo platelet activation, has also been reported. Steinberg et al., *N. Enql. J. Med.*, 317:1037–1042 (1987); Coller et al., *J. Clin. Invest.*, 73:794–799 (1984).

It has recently been found that a class of antigenic determinants are expressed when GPIIb-IIIa specifically binds to its ligand. The antigenic determinants are not expressed by either the non-occupied GPIIb-IIIa receptor or the non-bound ligand. One such determinant located on the C-terminus of the GPIIB heavy chain is recognized by the previously described PMI-1 monoclonal antibody. Shadle et al., *J. Cell Biol.*, 99:2056–2060 (1984); Frelinger et al., *J. Biol. Chem.*, 263:12397–12402 (1988).

BRIEF SUMMARY OF THE INVENTION

It has now been found that a portion of the C-terminus of hGPIIb, containing the PMI-1 antigenic determinant, becomes exposed upon receptor-ligand binding and is cleaved by indigenous proteases induced by thrombus formation to form a cleaved fragment. The fragment, referred to as C-terminal hGPIIb fragment, is released into the vascular fluid, and finds its way into other body fluids, such as urine.

Simple activation of platelets with agonists in vitro is not sufficient to release the C-terminal hGPIIb fragment. Treatment with a protease is required. In the thrombus, the platelet receptor is occupied, thereby exposing this region of the molecule, and a variety indigenous proteases, such as plasmin, are generated. Thus, in the present invention, detecting the release of C-terminal hGPIIb fragment by proteases is not subject to the problems of in vitro activation, and can be performed on a routinely obtained plasma or urine specimen from a patient.

The principal utility of the present invention is its ability to identify in vitro thrombotic events ongoing in vivo, and to monitor thrombolysis. Clinical settings include acute thrombotic events such as stroke or coronary thrombosis, or more chronic events such as deep venous thrombosis. In addition, detection of chronic ongoing thrombotic events can serve to identify individuals at risk of developing acute thrombosis.

The present invention is directed to a substantially isolated C-terminal hGPIIb fragment that has a molecular weight of about 3900 daltons, comprising an amino acid residue sequence that corresponds to the carboxy terminal portion of the amino acid residue sequence of hGPIIb shown in SEQ ID NO 1, including the amino acid residue sequence represented by the formula —IHPAHHK—, shown in SEQ ID NO 1 from residue 194 to residue 200. This fragment has the capacity to immunoreact with the monoclonal antibody PMI-1, and preferably has the amino acid residue sequence comprising the amino acid residue sequence shown in SEQ ID NO 1 from about residue 173 to about residue 200.

Also contemplated is a hGPIIb analog comprising a polypeptide of no more than about 200 residues, having an amino acid residue sequence that corresponds to the sequence of hGPIIb shown in SEQ ID NO 1 and includes at least about 7 contiguous amino acid residues from the amino acid residue sequence of hGPIIb shown in SEQ ID NO 1 from residue 173 to residue 200. A preferred analog is a polypeptide comprising an amino acid residue sequence corresponding to the formula: —PQPPVNPLK—; —PQPPVNLPLKVDWGLPIPSPSP—; —PLKVDWGLPIP—; —PIPSPSPIHPAHHK—; or —IHPAHHK — having a sequence shown in SEQ ID NO 1 from residue 173 to residue 181, from residue 173 to residue 193, from residue 179 to residue 189, from residue 187 to residue 200, or from residue 194 to residue 200.

Further contemplated is an antibody comprising an antibody molecule or fragment thereof that is capable of immunoreacting specifically with C-terminal hGPIIb fragment but does not substantially immunoreact with a polypeptide represented by the formula REQNSLDSWGPK having the sequence in SEQ ID NO 1 from residue 113 to residue 124. In preferred embodiments, the antibody composition contains a monoclonal antibody or fragment thereof that is substantially similar to the antibody, or fragment of the antibody, produced by hybridoma PMI-1.

The present invention also contemplates a method for assaying the presence of a C-terminal hGPIIb fragment in a body fluid sample. The method comprises admixing an aliquot of body fluid with an antibody of this invention. Contact of the body fluid and the antibody is maintained for a time period sufficient for an immunoreaction product to form. The fragment-containing immunoreaction product formed is then detected, thereby indicating the presence of the C-terminal hGPIIb fragment in the sample.

A diagnostic system in kit form is further contemplated by the present invention. In one embodiment is a diagnostic system in kit form for assaying for the presence of a C-terminal hGPIIb fragment in a body fluid sample. The system comprises a package containing, in an amount sufficient to perform at least one assay, an antibody of this invention. The antibody can be in a liquid solution but in one embodiment is preferably attached to a solid-phase matrix. The system may also contain a label for indicating the presence of the antibody molecules in the immunoreaction product formed.

In a more preferred embodiment, the diagnostic system further contains a solid support comprising a solid matrix having affixed thereto at least one of the set of hGPIIb analog and a polypeptide having an amino acid residue sequence that includes the sequence of a C-terminal hGPIIb fragment, thereby providing a kit for assaying by a competition ELISA a vascular fluid or urine sample for the presence of C-terminal hGPIIb fragment.

In one preferred embodiment, the before-described method is utilized to assess the extent of acute thrombosis by detecting the presence of C-terminal hGPIIb fragment in a body fluid sample and relating the amount of immunoreaction product formed to predetermined standards correlative with the diseased state.

In another preferred embodiment, this method is useful to monitor the course of plasminogen activator-induced thrombolysis by detecting the presence of C-terminal hGPIIb fragment in a body fluid sample and relating the amount to correlative predetermined levels.

In yet another preferred embodiment, this method is contemplated for identifying individuals at risk of developing acute thrombosis, which method determines the extent of chronic thrombosis and relates it to predetermined levels correlating with the risk of acute thrombosis.

BRIEF DESCRIPTION OF THE DRAWINGS

In the Figures forming a portion of the disclosure of this invention:

FIGS. 1A and 1B illustrates the effect of in vitro incubation of platelets at 37C in the presence of 30 uM chymotrypsin as described in Example 1c. One portion of the digested platelet suspension was centrifuged and the supernatant (open diamond) and resuspended pellet (+) were assayed separately. An equal portion of the platelet suspension was assayed comprising total PMI-1 immunoreactive material (open square). Levels of the PMI-1 epitope (FIG. 1A) or the Tab epitope (FIG. 1B) (a monoclonal antibody with a different GPIIb epitope specificity) were determined by competitive ELISA assays, as described hereinafter. Note the release of material reactive with PMI-1, but not with Tab, into the platelet-free supernatant.

DETAILED DESCRIPTION OF THE INVENTION

I. Definitions

Figure 1A:
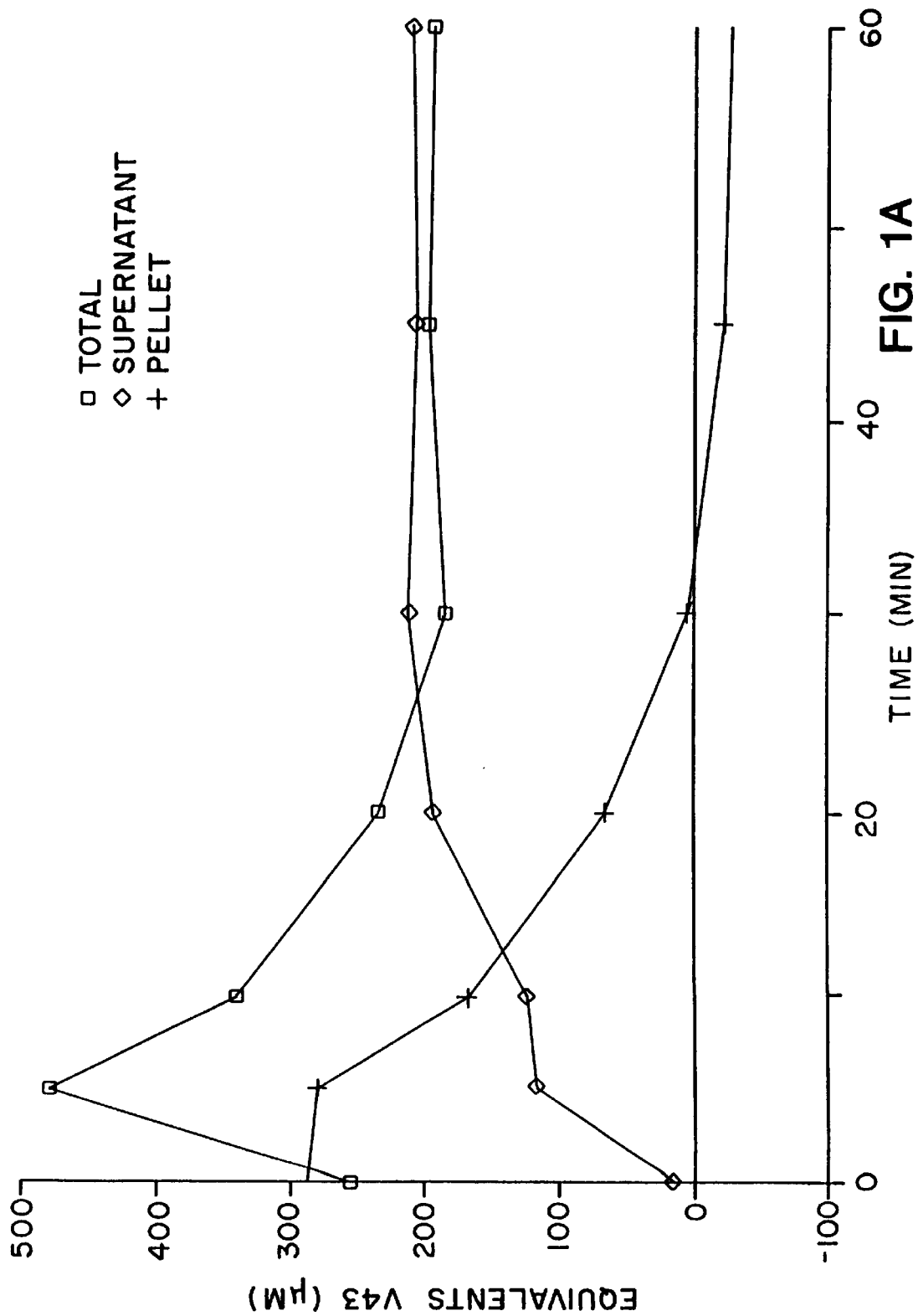

Amino Acid: An amino acid formed upon chemical digestion (hydrolysis) of a polypeptide at its peptide linkages. The amino acid residues identified herein are preferably in the natural "L" isomeric-configuration. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of the polypeptide. In keeping with standard polypeptide nomenclature, *J. Biol. Chem.*, 243:3557–59 (1969) and adopted at 37 C.F.R. 1.822(b)(2), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by have a left to right orientation in the conventional direction of amino-terminus to carboxy-terminus. In addition, the phase "amino acid residue" is broadly defined to include modified and unusual amino acids, such as those listed in 37 C.F.R. 1.822(b)(4), and are incorporated by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

II. Introduction

Platelets play a central role in thrombosis. The invention provides an in vitro means to detect platelet incorporation into thrombi in vivo, and thereby detects thrombotic events.

When platelets are incorporated into a thrombus, occupancy of GPIIb-IIIa receptor by its ligand is believed to expose the C-terminal region of the GPIIb heavy chain. Indigenous proteases, such as plasmin or leukocyte enzymes, generated at the site of the thrombus in vivo cleave the C-terminal portion of hGPIIb, releasing the small peptide fragments described above. Measurement of these fragments in vascular fluid or in urine provides a diagnostic correlate of the extent of the thrombotic process. These measurements are also valuable in monitoring the course of thrombolysis induced by plasminogen activators.

PMI-1, a monoclonal antibody derived from immunization of mice with isolated human platelet plasma membranes, reacts with the carboxy terminal aspect of the heavy chain of the platelet membrane glycoprotein hGPIIb. Shadle et al., *J. Cell Biol.*, 99:2056–2060 (1984); and Loftus et al., *Proc. Natl. Acad. Sci. USA*, 840:7114–7118 (1987). In the present invention, an enzyme-linked immunosorbent assay (ELISA) has been developed to measure levels of PMI-1 antigenic material. The principal observation, illustrated in FIGS. 1A and 1B, is that in vitro treatment of platelets with protease releases from the carboxy terminus of the GPIIb heavy chain a small (approximately 7 kDa, based on average MW of amino acid residue=120) fragment that contains the PMI-1 epitope. The fragment is referred to herein as the C-terminal hGPIIb fragment.

A potential site of cleavage of GPIIb-IIIa by indigeneous proteases is downstream from the cysteine residue at position 171 of the sequence shown in SEQ ID NO 1. The cysteine at position 171 participates in disulfide bridging to the light chain of GPIIb. Calvette et al., *Biochem. J.*, 261:551–560 (1989). The preferred site for chymotrypsin cleavage of GPIIb-IIIa when present on platelets is between residues 172 and 173 of the sequence shown in SEQ ID NO 1.

The carboxy terminus of hGPIIb has been identified by Loftus et al., *J. Biol. Chem.* 263:11025 (1988). After initial processing to cleave the GPIIb precursor protein into the heavy and light chain, alternate proteolytic processing results in partial trimming back of the carboxy terminus of hGPIIb. The partial proteolysis produces a polypeptide having either an lysine (K) or arginine (R) at the carboxy terminus, corresponding to residue 200 or 201, respectively, of the sequence shown in SEQ ID NO 1.

The capacity of the PMI-1 monoclonal antibody to inhibit platelet adhesion to collagen, Shadle et al., *J. Cell Biol.*, 99:2056–2060 (1984), its upregulation by chelation of divalent cations, Ginsberg et al., *J. Clin. Invest.*, 78:1103–1111 (1986), and by occupancy of GPIIb-IIIa with adhesive ligands, Frelinger et al., *J. Biol. Chem.*, 263:12397–12402 (1988), has been previously published by the applicants and is well known. There have, however, been no prior publications on the use of an ELISA technique for detecting this novel hGPIIb fragment as a means of identifying and evaluating thrombosis.

As discussed before, and reviewed by Ginsberg et al., in *Immunologic Analysis: Recent Progress in Diagnostic Labor. Immunol.*, Nakamura et al., Eds. Masson Publishing, USA Inc., 199–209 (1982), there have been numerous assays designed to quantitate released platelet granule components in the circulation as a means for detecting platelet activation. The present invention, however, does not involve release of a granule component, but rather involves the detection of a proteolytic attack on a platelet surface component, and as such is less susceptible to in vitro artifact, e.g., false positive results due to in vitro activation of platelets.

III. hGPIIb Fragment and Analogs

A. Fragment

In one embodiment, the present invention contemplates a substantially isolated C-terminal hGPIIb fragment having a molecular weight of about 3900 daltons, comprising an amino acid residue sequence that corresponds to the carboxy-terminal portion of the amino acid residue sequence of hGPIIb. The C-terminal hGPIIb fragment includes as a portion of its amino acid residue sequence the sequence represented by the formula —IHPAHHK— shown is SEQ ID NO 1 from residue 194 to residue 200, and has the capacity to immunoreact with the monoclonal antibody, PMI-1. Preferably, the C-terminal hGPIIb fragment has the amino acid residue sequence shown in SEQ ID NO 1 from about residue 173 to about residue 200.

A C-terminal hGPIIb fragment can be purified from human urine or plasma using well known immunoaffinity methods, such as described in Example 1c(2). Alternatively, C-terminal GPIIb fragment can be produced in vitro by proteolysis of platelets or by proteolysis of isolated GPIIb-IIIa, and subsequently immunoaffinity purified as described in Example 1. Proteolysis of platelets or isolated GPIIb-IIIa using the protease chymotrypsin is particularly preferred. The latter procedure is preferred due to the availability of platelets and the amount of GPIIb-IIIa contained therein.

C-terminal hGPIIb fragment is substantially isolated if compositions containing the fragment are comprised of greater than 5 percent, by weight, of fragment per total protein in the composition.

C-terminal hGPIIb fragment, once isolated, is useful to produce immunogen for raising antibody specific for the fragment, and for use in the diagnostic methods and systems for detecting the presence and amount of C-terminal hGPIIb fragment in body fluid samples, as disclosed herein.

B. Polypertide Analogs of the C-Terminal hGPIIb Fragment

One embodiment of the present invention contemplates a polypeptide that includes amino acid residue sequences capable of mimicking antigenic determinants expressed by the C-terminal hGPIIb fragment. The hGPIIb fragment-mimicking polypeptide is also referred to herein as an analog, or hGPIIb analog. A hGPIIb polypeptide analog of the present invention comprises an amino acid residue sequence that corresponds, and preferably is identical, to a portion of the hGPIIb sequence shown in SEQ ID NO 1 from residue 1 to residue 200. The hGPIIb analog is from about 7 to about 200 amino acid residues in length, preferably less than about 50, and more preferably less than 20 residues in length, and includes a minimum of about 7 contiguous residues of the hGPIIb amino acid residue sequence shown in SEQ ID NO 1 from residue 173 to residue 200.

In one preferred embodiment, a hGPIIb analog includes at least the following amino acid residue sequence:

—IHPAHHK—, representing the amino acid residues 194–200 shown in SEQ ID NO 1. In this embodiment, a hGPIIb analog is also capable of immunoreacting with the monoclonal antibody, PMI-1. The antibody PMI-1 is known to be immunospecific for (i.e., immunoreacts with) the minimum epitope —IHPAHHK— on hGPIIb.

In another embodiment, a preferred hGPIIb analog is a polypeptide that comprises an amino acid residue sequence corresponding to one of the following amino acid sequences:

—PQPPVNPLK—,
—PLKVDWGLPIP—,
—PIPSPSPIHPAHHK—, or
—IHPAHHK—, having an amino acid residue sequence shown in SEQ ID NO 1 from residue 173 to residue 181, from residue 179 to residue 189, from residue 187 to residue 200, or from residue 194 to residue 200, respectively.

Particularly preferred hGPIIb analogs are contemplated having an amino acid residue sequence as shown in Table 1 below.

TABLE 1

| Designation[a] | Amino Acid Residue Sequence |
|---|---|
| p173–193 | PQPPVNPLKVDWGLPIPSPSP |
| p173–181 | PQPPVNPLK |
| p179–189 | PLKVDWGLPIP |

TABLE 1-continued

| Designation[a] | Amino Acid Residue Sequence |
|---|---|
| p187–200 | PIPSPSPIHPAHHK |
| p194–200 | IHPAHHK |

[a]The designation of each polypeptide represents the included amino acid residue sequence as shown in SEQ ID NO 1.

One contemplated hGPIIb analog has an amino acid residue sequence that corresponds to the sequence shown in SEQ ID NO 1 from residue 1 to residue 200. More preferred is a hGPIIb analog that corresponds in sequence to a C-terminal hGPIIb fragment and has a sequence shown in SEQ ID NO 1 from residue 173 to residue 200.

The polypeptides shown in Table 1 are further characterized by their ability to neutralize (competitively inhibit) the binding of antibody molecules to their respective antigenic determinants on the native hGPIIb molecule, described hereinbelow.

It should be understood that a hGPIIb analog of the present invention need not be identical to the amino acid residue sequence of hGPIIb, so long as it has sufficient similarity with (i.e., corresponds to) portions of hGPIIb that the analog is able to competitively inhibit the immunoreaction of specific antibody molecules, elicited as described hereinbelow. Therefore, a hGPIIb analog can be subject to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue, such as isoleucine, valine, leucine or methionine for another, or the substitution of one polar residue for another, such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite immunoreaction activity.

When a polypeptide of the present invention has a sequence that is not identical to the corresponding sequence of hGPIIb because one or more conservative or non-conservative substitutions have been made, usually no more than about 20% and preferably no more than 10% of the amino acid residues are substituted, except where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, etc.

When coupled to a carrier via a linker to form what is known in the art as a carrier-hapten conjugate, a hGPIIb analog of the present invention is capable of inducing formation of antibodies that immunoreact with the C-terminal fragment of hGPIIb when present as a free-floating fragment in vascular fluid or urine.

In view of the well established principle of immunologic cross-reactivity, the present invention therefore contemplates antigenically related variants of the polypeptides described before. An "antigenically related variant" is a polypeptide that is capable of inducing formation of antibody molecules that immunoreact with a hGPIIb analog and with the C-terminal hGPIIb fragment when present in body fluids.

Any hGPIIb analog of the present invention can be synthesized by one of many techniques known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco (1969); Bodansky et al., "Peptide Synthesis", John Wiley & Sons, 2nd Ed., (1976); and Meienhofer, "Hormonal Proteins and Peptides", 2:46, Academic Press, New York (1983) for solid phase peptide synthesis; and Schroder et al., "The Peptides", Vol. 1, Academic Press, New York (1965) for classical solution synthesis, each of which is incorporated herein by reference. Appropriate protective groups usable in such synthesis are described in the above texts and in McOmie, "Protective Groups in Organic Chemistry", Plenum Press, New York (1973), which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid-phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting groups (and solid support) are removed sequentially or concurrently, to afford the final polypeptide.

A hGPIIb analog can be used, inter alia, in the diagnostic methods and systems of the present invention to detect C-terminal hGPIIb fragment present in a body sample, or can be used to prepare an inoculum as described herein for the preparation of antibodies that immunoreact with the fragment.

IV. Antibodies and Antibody Compositions

The term "antibody" in its various grammatical forms is used herein to refer to immunoglobulin molecules and fragments thereof, namely immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

The term "antibody combining site" refers to that structural portion of an antibody molecule, comprised of a heavy and light chain variable and hypervariable regions, that specifically binds (immunoreacts with) an antigen. The term "immunoreact" in its various forms is used herein to refer to binding between an antigenic determinant-containing molecule and a molecule containing an antibody combining site such as a whole antibody molecule or a portion thereof.

The term "antigenic determinant" refers to the actual structural portion of the antigen that is immunologically bound by an antibody combining site. The term is also used interchangeably with "epitope".

As used herein, the term "specifically bound" refers to a non-random binding reaction between an antibody and a antigen.

A. Antibody Compositions

An antibody composition of the present invention is characterized as containing antibody molecules that immunoreact with a C-terminal hGPIIb fragment or hGPIIb analog as described herein.

An antibody of this invention, i.e., an anti-C-terminal hGPIIb fragment antibody, does not immunoreact with other portions of the hGPIIb molecule, such as antigenic determinants defined by polypeptides corresponding in sequence to regions of hGPIIb that do not include residues 173 through 200 of the sequence shown in SEQ ID NO 1. Thus, for example, a contemplated antibody does not immunoreact with a polypeptide having a sequence represented by the formula REQNSLDSWGPK, shown in SEQ ID NO 1 from residue 113 to residue 124. That is, the antibody is specific for the C-terminal hGPIIb fragment identified and defined herein.

Thus an antibody, in its various embodiments, immunoreacts with an epitope present on a C-terminal hGPIIb fragment. Exemplary epitopes are defined by the C-terminal hGPIIb analogs designated p173-181, p179-189, p187-200 or p194-200. Additional epitopes can reside within the hGPIIb C-terminal fragment that are useful for defining the immunoreactivity of an antibody of this invention. Thus other embodiments contemplate an antibody that immunoreacts with a polypeptide defining regions other than the p194-200 portion of hGPIIb C-terminal fragment. Exemplary antibodies immunoreact with the polypeptide p173-193, shown in SEQ ID NO 1 from residues 173 to 193.

Such a contemplated antibody composition is typically produced by immunizing a mammal with an inoculum containing a C-terminal hGPIIb fragment of this invention, or a polypeptide analog, thereby inducing production in the mammal of antibody molecules having immunospecificity for the C-terminal hGPIIb fragment. The antibody molecules are then collected from the mammal and isolated to the extent desired by well known techniques such as, for example, by using DEAE SEPHADEX™ (dimethylaminoethyl sephadex) to obtain the IgG fraction. To enhance the specificity of the antibody, the antibodies may be purified by immunoaffinity chromatography using solid phase-affixed immunizing polypeptide or C-terminal hGPIIb fragment. The antibody is contacted with the solid phase-affixed immunizing polypeptide or fragment (immunogen) for a period of time sufficient for the immunogen to immunoreact with the antibody molecules to form a solid phase-affixed immunocomplex. The bound antibodies are separated from the complex by standard techniques.

Preferred and exemplary are the methods to produce and isolate antibodies described in Example 3.

The antibody composition so produced can be used inter alia, in the diagnostic methods and systems of the present invention to detect the presence and/or amount of C-terminal hGPIIb fragment in a body sample.

A preferred antibody in an antibody composition of this invention is a monoclonal antibody.

B. Inocula

The word "inoculum" in its various grammatical forms is used herein to describe a composition containing a polypeptide or the C-terminal hGPIIb fragment of this invention as an active ingredient used for the preparation of antibodies that immunoreact with the C-terminal hGPIIb fragment. The inoculum also contains a pharmaceutically acceptable aqueous diluent such that, when administered by immunization, is capable of eliciting antibodies that immunoreact with the hGPIIb C-terminal fragment.

When a polypeptide is used to induce antibodies it is to be understood that the polypeptide can be used alone, or linked to a carrier as a conjugate, or as a polypeptide polymer, but for ease of expression, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As discussed before, one or more additional amino acid residues can be added to the amino- or carboxy-termini of the polypeptide to assist in binding the polypeptide to a carrier. Cysteine residues added to the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodiimide technology, as in the use of a water-soluble carbodiimide to form amide links to the carrier. For a review of protein conjugation or coupling through activated functional groups, see Avrameas, et al., *Scand. J. Immunol.*, 1:7–23 (1978).

Useful carriers are well known in the art, and are usually proteins themselves. Examples of such carriers are keyhole limpet hemocyanin (KLH), edestin, thyroglobulin, albumins, such as bovine serum albumin (BSA) or human serum albumin (HSA), red blood cells, such as sheep erythrocytes (SRBC), tetanus toxoid, cholera toxoid as well as polyamino acids, such as poly (D-lysine: D-glutamic acid), and the like.

The choice of carrier is dependent upon the ultimate use of the inoculum and is based upon criteria not particularly involved in the present invention. For example, a carrier that does not generate an undesired reaction in the particular animal to be inoculated should be selected.

The inoculum contemplated herein contains an effective immunogenic amount of an immunogen of this invention, e.g., an hGPIIb analog or a C-terminal hGPIIb fragment, typically as a conjugate linked to a carrier. The effective amount of polypeptide or protein per unit dose sufficient to induce an immune response to the immunogen depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent or vehicle such as water, saline or phosphate-buffered saline to form an aqueous composition. Such diluents are well known in the art and are discussed, for example, in *Remington's Pharmaceutical Sciences*, 16th Ed., Mack Publishing Company, Easton, Pa. (1980) at pages 1465–1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

C. Monoclonal Antibody Compositions

The phrase "monoclonal antibody composition" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495–497 (1975), which description is incorporated by reference. Detailed preparation of a monoclonal antibody composition is described further herein.

Thus, a monoclonal antibody of this invention immunoreacts with a C-terminal hGPIIb fragment or hGPIIb analog of this invention, but does not substantially immunoreact with a polypeptide having a sequence represented by the formula REQNSLDSWGPK shown in SEQ ID NO 1 from residue 113 to residue 124. That is, the antibody is specific for the C-terminal hGPIIb fragment.

Particularly preferred is a monoclonal antibody that immunoreacts with a hGPIIb analog of this invention, particularly the polypeptide IHPAHHK or polypeptides that contain the sequence —IHPAHHK— shown in SEQ ID NO 1 from residues 194 to 200. Exemplary of this preferred embodiment is the monoclonal antibody PMI-1, available from the American Type Culture Collection 10801 University Blvd., Manassas, Va. 20110-2201 (ATCC, Rockville, Md.) and having ATCC accession number HB 9476, that has been shown to be immunospecific for an epitope on hGPIIb defined by the polypeptide IHPAHHK and present on a C-terminal hGPIIb fragment.

In a related embodiment a monoclonal antibody is contemplated that immunoreacts with a hGPIIb analog defined by a polypeptide comprising a sequence of amino acid residues shown in SEQ ID NO 1 from residues 173 to 193, particularly a polypeptide having the sequence shown in SEQ ID NO 1 from residues 173 to 181, from residues 179 to 189, or from residues 179 to 193.

V. Methods for Producing Monoclonal Antibody Compositions

The present invention contemplates a method of forming a monoclonal antibody molecule that (a) immunoreacts with an antigenic determinant (epitope) on the C-terminal hGPIIb fragment, said fragment including an amino acid residue sequence as shown in SEQ ID NO 1 from residues 173 to 200, from residues 173 to 181, from residues 173 to 193, from residues 179 to 189, from residues 179 to 193, or from residues 194 to 200, but (b) does not substantially immunoreact with a polypeptide represented by the formula REQNSLDSWGPK shown in SEQ ID NO 1 from residues 113 to 124.

A preferred method comprises the steps of:

(a) Immunizing an animal with an inoculum containing a C-terminal hGPIIb fragment or a polypeptide hGPIIb analog as described herein as the immunogen. Preferably, the immunogen is complexed with a carrier or immunopotentiator such as an ISCOM particle, liposome or the like. The inoculum is administered to an immunologically competent mammal in an amount sufficient to produce an immune response. Preferably, the mammal is a rodent such as a rabbit, rat or mouse. The mammal is then maintained for a time period sufficient for it to produce cells secreting antibody molecules that immunoreact with the C-terminal hGPIIb fragment.

(b) Preparing a suspension of immune cells. This is typically accomplished by removing the spleen of the mammal and mechanically separating the individual spleen cells in a physiologically tolerable medium using methods well known in the art.

(c) Treating the suspended antibody-producing cells with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/O-Ag14, that are available from the ATCC under the designations CRL 1580 and CRL 1581, respectively, and the like.

In preferred embodiments, treatment with the transforming agent results in the production of a hybridoma by means of fusing the suspended spleen cells with mouse myeloma cells from a suitable cell line by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art can be employed.

The cell line used should preferably be of the so-called "drug resistant" type, so that unused myeloma cells will die in a selective medium, whereas hybrids will survive. The most cell lines used for this purpose are 8-azaguanine resistant. These lines lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "Non-secreting" type, i.e., does not itself produce antibody molecules. In certain cases, however, secreting myeloma lines may be preferred.

(d) Cloning the transformed cells, preferably to monoclonality. The cloning is preferably performed in a tissue culture medium that will not sustain (support) non-transformed cells. When the transformed cells are hybridomas, this is typically performed by diluting and culturing in separate containers the mixture of unused spleen cells, unused myeloma cells, and fused cells (hybridomas) in a selective medium which will not sustain the unused myeloma cells. The cells are cultured in this medium for a time sufficient to cause death of the unused cells (about one week). The dilution can be a limiting dilution, in which the volume of diluent is statistically calculated to isolate a certain number of cells (e.g., 1–4) in each separate container (e.g., each well of a microtiter plate). The medium is one (e.g., HAT medium) that will not sustain the drug-resistant (e.g., 8-azaguanine resistant) unused myeloma cell line.

(e) Screening the tissue culture medium of the cloned transformants to detect the presence of secreted antibody molecules as discussed in Example 4a. Preferably, the medium is monitored using well known immunological techniques for the appearance of antibody molecules that immunoreact with C-terminal hGPIIb fragment.

(f) Selecting a desired transformant and growing it in an appropriate tissue culture medium for a suitable length of time, and harvesting the antibody from the culture supernatant by well known techniques. The suitable medium and suitable length of culturing time are also well known or are readily determined.

A monoclonal antibody of the present invention can also be produced by preparing a culture containing a monoclonal hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Representative and preferred methods for producing monoclonal antibody compositions of this invention are described in Example 3c.

To produce a much greater concentration of slightly less pure monoclonal antibody, the selected hybridoma can be transferred by injection into mice, preferably syngeneic or semisyngeneic mice. The hybridoma will cause formation of antibody-producing ascites tumors after a suitable incubation time, which will result in a high concentration of the desired antibody (about 5–20 mg/ml) in the bloodstream and peritoneal exudate of the host mouse.

Media and animals useful for the preparation of these compositions are both well known in the art and commercially available and include synthetic culture media, inbred mice and the like. One commonly used synthetic medium is Dulbecco's minimal essential medium [DMEM; Dulbecco et al., *Virol.* 8:396 (1959)] supplemented with 4.5 gm/l glucose, 20 mM glutamine, and 20% fetal calf serum. A typical inbred mouse strain is the Balb/c.

The monoclonal antibody compositions produced by the above method can be used in the same manner as disclosed herein for antibodies of this invention, and are preferred.

For example, the monoclonal antibody can be used in the diagnostic methods and systems disclosed herein where formation of a C-terminal hGPIIb fragment-containing immunoreaction product is desired.

VI. Hybridomas

Hybridomas of the present invention are those characterized as having the capacity to produce an anti-GPIIb C-terminal fragment monoclonal antibody as described before.

Representative preferred hybridomas are prepared as described in Example 3. Particularly preferred is the hybridoma culture designated PMI-1.

Hybridoma culture PMI-1 has been deposited pursuant to Budapest Treaty requirements with the American Type Culture Collection (ATCC), Rockville, Md., on May 17, 1989, and was assigned accession number HB 9476.

Hybridoma HB 9476 was deposited in a depository affording permanence of the deposit and ready accessibility thereto by the public upon the issuance of a patent, under conditions which assure that access to the hybridoma will be available during the pending of the patent application to those deemed by the Commissioner to be entitled to such access, and that all restrictions on the availability to the public of the hybridoma as deposited will be irrevocably removed upon the granting of the patent. The deposited hybridoma will be maintained by the ATCC for the term of the patent or 30 years from the date of deposit, whichever is longer, and in all events for at least five years after the date of the last request for access. All maintenance fees have been paid.

Methods for producing hybridomas secreting antibody molecules having a desired immunospecificity, i.e., having the ability to immunoreact with a particular protein, an identifiable epitope on a particular protein and/or a polypeptide, are well known in the art and are described further herein. Particularly applicable is the hybridoma technology described by Niman et al., *Proc. Natl. Acad. Sci. USA*, 80:4949–4953 (1983), and by Galfre et al., *Meth. Enzymol.*, 73:3–46 (1981), which descriptions are incorporated herein by reference.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci.*, 86:5728–5732 (1989); and Huse et al., *Science*, 246:1275–1281 (1989).

Also contemplated by this invention is the hybridoma cell, and cultures containing a hybridoma cell that produce a monoclonal antibody of this invention.

VII. Diagnostic Systems

A diagnostic system of the present invention in kit form includes, in an amount sufficient to perform at least one assay, a composition containing polyclonal or monoclonal antibody of this invention or fragments thereof, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like. Also included, in one form or another, may be charts, graphs and the like that demonstrate predetermined concentration levels correlating specific physiological conditions to thrombotic events.

A diagnostic system is contemplated for assaying for the presence, and preferably amount, of C-terminal hGPIIb fragment in a body fluid sample, such as blood, plasma or urine according to the diagnostic methods described herein.

Preferably, the antibody is present as a monoclonal antibody composition, comprising a monoclonal antibody as described herein.

A diagnostic system of the present invention typically also includes a label or indicating means capable of signaling the formation of a specifically bound complex containing an antibody molecule of the present invention.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein iosthiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB200 SC) and the like. A description of immunofluorescence analysis techniques is found in DeLuca "Immunofluorescence Analysis", in *Antibody As A Tool*, Marchalonis et al., eds., John Wiley & Sons, Ltd., pp. 189–231 (1982) which is incorporated herein by reference.

In preferred embodiments, the indicating group is an enzyme, such as horseradish peroxidase (HRO), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabelling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labelling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such as $^{111}$indium of $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Avrameas, et al., *Scand. J. Immunol.*, Vol. 8, Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself an antibody molecule of the present invention. Exemplary specific binding agents are antibody molecules, complement proteins or fragments thereof, protein A and the like. Preferably, the specific binding agent can bind the antibody molecule of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of C-terminal hGPIIb fragment in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference. An exemplary ELISA protocol is described in Example 4.

Thus, in preferred embodiments, the antibody or antigen reagent component can be affixed (operatively linked) to a solid matrix to form a solid support that is separately packaged in the subject diagnostic systems. The reagent is typically affixed to the solid matrix by adsorption from an aqueous medium, although other modes of affixation, well known to those skilled in the art, can be used. Exemplary affixation methods are described in Example 4.

Particularly preferred are embodiments suitable for competition ELISA assays wherein the antibody is in the liquid phase together with a sample containing an unknown amount of C-terminal hGPIIb fragment and the antigen is in the solid phase in an amount sufficient to compete with liquid phase antigen for immunoreaction with the liquid phase antibody. In this embodiment, which is described in Example 4, the antigen can be hGPIIb analog, C-terminal hGPIIb fragment, or isolated GPIIb-IIIa.

Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

Thus, in particularly preferred embodiments, a diagnostic kit further contains, in a separate package, an antigen as described above for use in a the competitive ELISA assay in the form of a solid phase antigen as defined above.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

VIII. Assay Methods

The present invention contemplates any diagnostic method that results in detecting C-terminal hGPIIb fragment in a body fluid sample using an hGPIIb analog, a substantially isolated C-terminal hGPIIb fragment or an antibody of this invention as a reagent to form an immunoreaction product whose amount relates, either directly or indirectly, to the presence, and preferably amount, of C-terminal hGPIIb fragment in the sample.

Those skilled in the art will understand that there are numerous well known clinical diagnostic chemistry procedures in which an immunochemical reagent of this invention can be used to form an immunoreaction product whose amount relates to the amount of C-terminal hGPIIb fragment present in a body sample. Thus, while exemplary assay methods are described herein, the invention is not so limited.

Various heterogeneous and homogeneous protocols, either competitive or noncompetitive, can be employed in performing an assay method of this invention.

Generally, to detect the presence of a C-terminal hGPIIb fragment in a patient, an aliquot (i.e., a predetermined amount) of a body fluid sample, such as urine or a vascular fluid, namely blood, plasma or serum from the patient is contacted by admixture (admixed), with an antibody composition of the present invention to form an immunoreaction admixture. The admixture is then maintained under biological assay conditions for a period of time sufficient for the C-terminal hGPIIb fragment present in the sample to immunoreact with (immunologically bind) a portion of the antibody combining sites present in the antibody composition to form a C-terminal hGPIIb fragment-antibody molecule immunoreaction product (immunocomplex). The complex can then be detected as described herein. The presence of the complex is indicative of C-terminal hGPIIb fragment in the sample.

Maintenance time periods sufficient for immunoreaction are well known and are typically from about 10 minutes to about 16–20 hours at a temperature of about 4C to about 45C, with the time and temperature typically being inversely related. For example, longer maintenance times are utilized at lower temperatures, such as 16 hours at 4C, and shorter times for higher temperatures, such as 1 hour at room temperature.

Biological assay conditions are those that maintain the biological activity of the immunochemical reagents of this invention and the C-terminal hGPIIb fragment sought to be assayed such that the reagents retain their ability to form an immunoreaction product. Those conditions include a temperature range of about 4C to about 45C, a pH value of about 5 to about 9 and an ionic strength varying from that of distilled water to that of about one molar sodium chloride. Methods for optimizing such maintenance time periods and biological assay conditions are well known in the art.

Preferred maintenance times and assay conditions sufficient for immunoreaction to occur are described in Example 4.

According to the discoveries described herein, thrombosis is accompanied by the cleavage of the carboxy terminus of hGPIIb by indigenous proteases, to form soluble C-terminal hGPIIb fragment in body fluid samples. Thus, in one embodiment, the detection of C-terminal hGPIIb fragment in a body sample is utilized as a means to monitor the presence of an in vivo thrombic event in a patient (thrombosis) using an antibody molecule specific for the C-terminal hGPIIb fragment as disclosed herein.

In preferred embodiments, immunoassay of C-terminal hGPIIb fragment is conducted using a cell free body fluid sample. By cell free is meant that the sample does not contain detectable amounts of cells, tissue or other macroscopic biological materials normally present in a body fluid such as blood. A body fluid sample typically contains cells as a normal component, or as a contaminant, and can be rendered cell-free by a variety of biochemical procedures including centrifugation, filtration and chromatography, so long as the retained fluid sample contains substantially all of the soluble protein initially present in the sample prior to removal of the cells. Particularly preferred are centrifugation steps such as described in Example 4.

Thus a body fluid sample, such as blood, known to contain both platelets having GPIIb-IIIa thereon and soluble C-terminal hGPIIb fragment, is preferably treated, prior to admixing, to a manipulation that results in forming a cell-free body fluid sample, ie, separating the cells present in the sample away from the body fluid sample to form a cell-free body fluid sample. An aliquot of the cell-free body fluid sample is then admixed with an antibody of the invention to form an immunoreaction admixture.

Alternatively, the separation of C-terminal hGPIIb fragment from cells having GPIIb, such as platelets, may be accomplished at other stages of the assay methods disclosed herein. For example, the immunoreaction product containing C-terminal hGPIIb fragment can be separated from platelets present in the body fluid sample by centrifugation after the maintenance step under conditions that separate cells, i.e., platelets, from protein complexes such as an immunocomplex between C-terminal hGPIIb fragment and an antibody of this invention.

Determining the presence or amount of C-terminal hGPIIb fragment-containing immunoreaction product formed by the above maintenance step, either directly or indirectly, can be accomplished by assay techniques well known in the art, and typically depend on the type of indicating means used.

In a preferred competition assay method, the immunoreaction admixture described above further contains a solid phase having affixed thereto a solid phase antigen comprising a hGPIIb analog or a polypeptide having an amino acid residue sequence that includes the sequence of a C-terminal hGPIIb fragment of this invention. Thus, in this embodiment, the assay comprises the steps of:

(a) admixing a body fluid sample with 1) an antibody composition of this invention and 2) a solid support having affixed thereto (operatively linked) a hGPIIb analog or a polypeptide having an amino acid residue sequence that includes the sequence of a C-terminal hGPIIb fragment of this invention, or both, to form an immunoreaction admixture having both a liquid phase and a solid phase;

(b) maintaining said immunoreaction admixture under biological assay conditions for a time period sufficient to form an immunoreaction product in the solid phase; and (c) detecting the presence, and preferably amount, of the immunoreaction product formed in the solid phase in step (b), and thereby the amount of presence/amount of C-terminal hGPIIb fragment in the body fluid sample.

Where an hGPIIb analog is used in the solid phase, the antibody composition contains antibody molecules that immunoreact with the hGPIIb analog. Preferably, the solid phase antigen is isolated GPIIb-IIIa, prepared as described in Example 1b, or substantially isolated C-terminal hGPIIb fragment, prepared as described in Example 1c.

Preferably, the body fluid sample is a cell free body fluid sample such as urine or platelet poor plasma.

More preferably, detecting in step (c) is performed by the steps of:

(i) admixing the immunoreaction product formed in step (b) with an indicating means to form a second reaction admixture;

(ii) maintaining the second reaction admixture for a time period sufficient for said indication means to bind the immunoreaction product formed in step (b) and form a second reaction product; and, (iii) determining the presence and/or amount of indicating means in the second reaction product, and thereby the presence of the immunoreaction product formed in step (b). Particularly preferred is the use of a labeled second antibody, immunospecific for the first antibody, as the indicating means, and preferably the label is horseradish peroxidase. In one embodiment, it is particularly preferred to use (1) isolated GPIIb-IIIa as the solid phase antigen, (2) PMI-1 monoclonal antibody in the antibody composition, and (3) goat anti-mouse IgG antibodies labeled with horseradish peroxidase as the indicating means. Exemplary is the competition ELISA format described in Example 4.

In another competition assay format the immunoreaction admixture contains (1) a body fluid sample, preferably cell free, (2) an antibody of this invention and (3) a labeled hGPIIb analog or labeled C-terminal hGPIIb fragment, wherein the antibody is present in the solid phase, being affixed to a solid support, to form a liquid and a solid phase. In this embodiment, the admixed body fluid sample competes with the labeled reagent for immunoreaction with the solid phase antibody to form a solid phase immunoreaction product. Thereafter, the detection of label in the solid phase correlates with the amount of C-terminal hGPIIb fragment in the admixed fluid sample.

The following examples are intended to illustrate, but not limit, the present invention.

EXAMPLES

1. Preparation of Substantially Isolated C-Terminal hGPIIb Fragment a. Platelet Isolation One unit of whole human blood was collected in ACD (0.065 M citric acid, 0.085 M sodium citrate, 2% dextrose) containing hirudin (Sigma Chemical Co., St. Louis, Mo.) at a final concentration of 0.06 units per milliliter (U/ml) and centrifuged for 15 minutes (min) at 120×g. The resulting supernatant, designated platelet-rich plasma (PRP), was recovered, isolated and further centrifuged for 15 min at 1200×g to form a pellet of isolated platelets. The supernatant formed was collected and designated platelet-poor plasma (PPP).

b. GPIIb-IIIa Isolation from Platelets

A platelet pellet prepared as in Example 1a, was resuspended in 5 ml TBS (0.15 M NaCl, 0.2 M Tris, pH 7.4, $5 \times 10^{-4}$ M $CaCl_2$, $10^{-5}$ M leupeptin) and sonicated on ice for 10 min at a maximum setting using a Model W-375 sonicator (Heat Systems Ultrasonics, Plainview, N.Y.). The sonicated suspension was twice frozen and thawed using a dry ice-methanol ice bath and stored at minus 20 degrees C (20C). The frozen-thawed platelet sonicate was layered on top of 5 ml of a sucrose solution (40% v/v in TBS), and centrifuged at 4 degrees C for one hour at 38,000 rotations per minute (RPM) in a SW41 centrifuge rotor (Beckman Instruments, Fullerton, Calif.) to form a milky colored infranatant. The milky-infranatant was then recovered and centrifuged at 43,000 RPM in a SW50.1 centrifuge rotor (Beckman) at 4C for one hour. The resulting pellet was resuspended in typically 1–2 ml TBS to form a platelet membrane solution, the protein concentration of which was determined to be in the range of 10–25 mg/ml, typically using the Bio-Rad Protein Assay Kit (Bio-Rad, Richmond, Calif.) according to the manufacturer's instructions.

The platelet membrane solution was again centrifuged in a SW50.1 centrifuge rotor as above and the resulting pellet was resuspended in 2 ml of extraction buffer (0.03 M Tris, pH 7.4, $1 \times 10^{-5}$ M leupeptin, 200 mM n-octyl-beta-D-glucopyranoside; Calbiochem-Behring, La Jolla, Calif.). The platelet membrane extract thus formed was admixed thoroughly by vortexing and then maintained at room temperature for 30 min. The extract was thereafter centrifuged at 45,000 rpm in a SW50.1 centrifuge rotor for 1 hour at 4C and the platelet membrane extract supernatant thus formed was recovered.

The recovered supernatant was applied to a LKB Ultrogel Aca 34 gel filtration column (3×97 cm, LKB Instruments, Gaithersburg, Md.) that had been equilibrated with 1 liter of column buffer (0.03 M Tris, pH 7.4, 0.1 mM $CaCl_2$, 0.1% n-octyl-beta-D-glucopyranoside) and 5 ml fractions were collected from the resulting column effluent. The optical density at 280 nanometers of each fraction was determined and fractions around the several peaks were combined to form a pool for each peak. Samples from each pool were analyzed by electrophoresis in 6% polyacrylamide slab gels using the reducing buffers and procedures described by Laemmli, *Nature (London)*, 227:680–685 (1970), and low molecular weight protein standards ranging in size from 14.4 kilodaltons (kDa) to 92.5 kDa (Bio-Rad, Richmond, Calif.). The pool containing predominantly two protein species having molecular weights corresponding to GPIIb and GPIIIa, i.e., 120 kDa and 100 kDa, respectively was recovered and is designated as a composition containing isolated GPIIb-IIIa. The protein concentration of the isolated GPIIb-IIIa containing-composition thus prepared was typically determined using the Bio-Rad Protein Assay Kits to be in the range of 0.3 to 0.8 mg/ml.

c. Isolation of Carboxy-Terminal Fragment of hGPIIb from Platelets (1) Digestion with Proteases A platelet pellet prepared as in Example 1a was resuspended in Tyrode's solution (Sigma; 137 mM NaCl, 2 mM KCl, 12 mM $NaHCO_3$, 0.3 mM $NaH_2PO_4$, 2 mM $CaCl_2$, 1 mM $MgCl_2$, 5.5 mM glucose, 5 mM HEPES, pH 7.4) supplemented with 100 nM PGE1 (Sigma; prostaglandin inhibitor of activation), apyrase (Sigma)(primary suspension contained 7.5 ug/ml of PRP; washes contained 25 ug/ml), and BSA, 3.5 mg/ml. After two centrifugations in supplemented Tyrode's, the platelet concentration was adjusted to $1 \times 10^9$ per ml in supplemented Tyrode's. Alpha-chymotrypsin (Sigma) was added to produce a final concentration of 0.75 mg/ml and the solution was incubated for 60 min at 37 degrees C. The reaction was then stopped by adding a 200 mM stock solution of phenylmethylsulfonyl fluoride (PMSF) to form a final concentration of 1.0 mM PMSF in the platelet suspension.

During the time course of the 1 hour chymotrypsin incubation of the platelet suspension, aliquots of 0.2 ml containing $2 \times 10^8$ platelets were taken and processed further. A first aliquot (0.2 ml) of platelet suspension was centrifuged at 15,000×g for 5 min at room temperature to form a supernatant and a pellet. The supernatant was collected to form a supernatant sample. The pellet was resuspended in 0.2 ml of supplemented Tyrode's containing 1 mM PMSF to form a resuspended pellet sample for use in the ELISA assay described in Example 4b. A second aliquot (0.2 ml) of platelet suspension was used directly as a total sample in the ELISA assay of Example 4b. The presence, if any, of C-terminal hGPIIb fragment was then measured in the three samples (supernatant sample, resuspended pellet sample, and total sample extract) using the competition ELISA assay described in Example 4b.

The results are shown in FIG. 1, and indicate the levels of the PMI-1 epitope (FIG. 1A) and the levels of the TAB epitope (FIG. 1B) in the three fractions. Monoclonal antibody PMI-1 immunoreacts with the PMI-1 epitope on hGPIIb defined by the polypeptide IHPAHHK. Monoclonal antibody TAB immunoreacts with the TAB epitope located on a portion of hGPIIb other than the C-terminal hGPIIb fragment, because the material immunoreactive with TAB does not become released into the supernatant after chymotrypsin digestion.

(2) Isolation of C-Terminal hGPIIb Fragment

Isolated PMI-1 antibody molecules prepared as described in Example 3c, are covalently linked to Sepharose beads using cyanogen bromide-activated Sepharose (Pharmacia) according to the manufacturer's instructions to form PMI-1 SEPHAROSE™ having about 20 mg of antibody protein per ml of packed beads.

Five ml of chymotrypsin digested platelet suspension, prepared as in Example 1c(1), is admixed with 5 ml of packed PMI-1 Sepharose beads and the resulting admixture is maintained at 4 C for 12–18 hours to allow any C-terminal hGPIIb fragment in the suspension to bind to the PMI-1 Sepharose. The PMI-1 Sepharose is then transferred to a column containing a scintered glass support, and washed with 25 ml of wash buffer (described in Example 4), also containing 50 mM octylglucoside. Thereafter wash buffer containing 50 mM octylglucoside is added to the column and 1.25 ml fractions are collected as the added buffer comes off (elutes from) the column to form eluted fractions.

Fifty microliters (ul) of each eluted fraction is then analyzed by sodium dodecylsulfate (SDS) polyacrylamide gel electrophoresis (SDS-PAGE) using a 10–20% acrylamide gel gradient containing 3% SDS and 5% 2-mercaptoethanol according to the methods of Laemmli, *Nature*, 227:680–685 (1970). Proteins contained in the eluted fractions so analyzed are transferred from the SDS-PAGE gels to nitrocellulose and visualized by autoradiography according to the method of Johnson et al, *Gen. Anal. Techn.*, 1:3–8 (1984) using $^{125}$I-labeled PMI-1. The apparent molecular weight of the visualized proteins is determined by comparison to protein molecular weight markers also analyzed on the gel. All molecular weights are in units of one thousand daltons.

Fractions containing eluted proteins that reacted with PMI-1 antibody are collected and pooled to form an isolated C-terminal hGPIIb fragment-containing solution, i.e., substantially isolated hGPIIb fragment. The isolated protein exhibited an apparent weight of about 3,900 daltons when analyzed by SDS-PAGE, and constituted the major protein component in the isolated fragment-containing solution.

The amino acid residue sequence of the C-terminal hGPIIb fragment identified herein after in vitro proteolysis of platelets is shown in SEQ ID NO 1 from residue 173 to residue 200.

2. Preparation of Polypeltide Analogs

Based on the amino acid residue sequence deduced from the nucleotide sequence of hGPIIb, polypeptides corresponding to the various hGPIIb C-terminal regions utilized herein are chemically synthesized on an Applied Biosystems Model 430A Peptide Synthesizer using the symmetrical anhydride method of Hagenmaier, et al., *Hoppe-Seyler's Z. Phisiol. Chem.*, 353:1973 (1982).

The amino acid residue sequences of the various polypeptide analogs synthesized are shown in Table 1.

3. Antibody Production a. Preparation of Immunogen

The term "immunogen", as used herein, describes an entity that induces antibody production in the host animal. In some instances, the antigen and immunogen are the same entity, while in other instances, the two entities are different. Immunogens used to elicit antibodies of this invention are whole platelets, platelet membranes, isolated GPIIb-IIIa, isolated C-terminal hGPIIb fragment or hGPIIb polypeptide analogs as described above.

Polyclonal anti-peptide antibodies are produced by immunizing rabbits with a peptide prepared in Example 2 above and coupled to carrier protein. Coupling of the peptide with glutaraldehyde to thyroglobulin as antigenic carrier (Bovine Type I, Sigma Chemical Co., St. Louis, Mo.) is conducted as described by J. G. Dockray, *Regulatory Peptides*, 1:169–186 (1980), which is hereby incorporated by reference to form thyroglobulin coupled peptide.

b. Preparation of Polyclonal Antibody Compositions

Immunizations to produce a polyclonal antibody composition are done according to standard protocols. Briefly, a rabbit is immunized intradermally at one week intervals with 400 micrograms (ug) of immunogen consisting of thyroglobulin coupled peptide at 3 mg/ml. The immunogen is diluted 1:1 in Complete Freund's Adjuvant for the first immunization, in Incomplete Freund's Adjuvant for the second and third immunizations, and in normal saline for the fourth and fifth.

Injections are administered with 100 ug distributed over 4 sites. Thereafter, the antibody is harvested and tested according to the assay of Example 4a. In that assay, polyclonal antibody produced using a peptide of Table 1 immunoreacts with the carboxy terminal hGPIIb fragment and with the immunizing peptide, but does not immunoreact with the polypeptide REQNSLDSWGPK.

c. Preparation of Monoclonal Antibody Compositions

Monoclonal antibodies that immunoreact with C-terminal hGPIIb fragment were produced using standard hybridoma technology with exceptions as noted. Balb C mice were immunized biweekly with 50 ug of platelet membranes prepared as described by Barber et al., *J. Biol. Chem.*, 245:6357–65 (1970), incorporated herein by reference, emulsified alternately in complete and incomplete Freund's adjuvant. Mice were bled from the retro-orbital plexus, and sera were screened for antibodies by solid-phase radioimmunoassay as described in Shadle et al., *J. Cell Biol.*, 99:2056–2060 (1984). Three days after the fifth immunization, about $1 \times 10^8$ lymphocytes were isolated from the spleens of mice, admixed into a suspension and fused with $5 \times 10^7$ P3X63AG8.053 mouse myeloma cells using 50% PEG 4000 as the cell fusion promoter. The resultant transformed (fused) antibody-producing cells (hybridomas) were initially transferred to 96-well microtiter plates at a density of about $1 \times 10^6$ cells per well and cultured in selective HAT medium.

Tissue culture supernatant appearing to contain viable HAT resistant hybridoma cells after 8 days of culturing were screened in the ELISA assay described in Example 4a for the presence of antibody molecules that immunoreact with GPIIb-IIIa prepared as described in Example 1b. Hybridoma cultures were identified that produced GPIIb-IIIa-immunoreacting antibody molecules. The isolated hybridomas were then subcloned twice at limiting dilutions to provide about 1 cell per well and 24 of the resultant hybridoma cultures were shown to be of monoclonal origin on the basis of three criteria: (1) each supernatant was from a single cell focus and immunoreacted with GPIIb-IIIa in the ELISA screen, (2) each supernatant showed a single homogeneous band when analyzed by cellulose acetate gel electrophoresis according to the method described in *Monoclonal Antibodies: Principles and Practice*, J. W. Goding, ed., Academic Press, Inc., Orlando, Fla., 1983, and (3) each supernatant contained a single isotype of immunoglobulin when analyzed using the Mouse Ig Screening and Isotyping Kit according to the instructions provided by the manufacturer, Boehringer-Mannheim Biochemicals, Indianapolis, Ind.

One monoclonal antibody producing hybridoma, PMI-1, isolated by the above procedure using an inoculum containing platelet membranes is available from the ATCC and has an accession number HB 9476.

A culture of hybridoma cells capable of secreting PMI-1 monoclonal antibodies were introduced into a mouse and the ascites fluid was then harvested as is well known. PMI-1 monoclonal antibody molecules present in the harvested ascites were isolated using protein-A Sepharose (Pharmacia, Piscataway, N.J.) according to the manufacturer's instructions to form isolated PMI-1 antibody molecules.

The protein concentration of isolated antibody molecules in a liquid composition was determined, as needed, using the Bio-Rad Protein Assay Kit (Bio-Rad, Richmond, Calif.) according to the manufacturer's instructions.

To prepare a monoclonal antibody composition containing $^{125}$I-labeled antibody molecules, 350 microliters (ul) of PBS (0.15 M NaCl, 0.01 M sodium phosphate, pH 7.09) containing 1 milligram per milliliter (mg/ml) of the above isolated PMI-1 antibody molecules were admixed with 40 micrograms (ug) of chloramine-T and 1 millicurie (mCi) of carrier-free Na$^{125}$I (Amersham, Arlington Heights, Ill.). The resulting admixture was maintained for 5 minutes at about 20C and then admixed with 20 ul of a 2 mg/ml sodium metabisulfite solution (2 mg/ml) and 20 ul of a potassium iodide solution. Thereafter, 800 ul of PBS containing 1% BSA were admixed followed by further admixture of diisopropylfluorophosphate to a final concentration of 10 mM. The resulting admixture was maintained for 60 minutes at 22 C and then dialyzed against PBS. The specific activity of the resulting $^{125}$I-labeled antibody molecules was about 4.5 microcurie (uCi) per ug.

Compositions containing Fab fragments were prepared by digesting isolated PMI-1 antibody molecules with papain (200:1 weight per weight of Ig to papain) for 6 hours at 37° C. following the methods of Mage et al., *Methods in Enzymology*, 70:142–150 (1980). Undigested Ig and Fc fragments were removed by chromatography on protein A-Sepharose. The resulting Fab fragments-containing compositions were then ready for use, or were $^{125}$I-labeled, as needed, using the same procedures as described above for monoclonal antibody compositions.

4. Diagnostic Assays a. ELISA To Screen Monoclonal Antibodies

Antibody molecules contained in hybridoma culture supernatant are examined for their ability to immunoreact with hGPIIb polypeptide analogs. Fifty microliters (ul) of coating solution (0.1M NaHCO$_3$, pH 8.0, 0.1% NaN$_3$) containing 10 ug/ml of polypeptide analogs prepared in Example 2 are admixed into the wells of flat-bottom 96-well microtiter plates (Immulon 2; Dynatech Laboratories, Chantilly, Va.). The plates are then maintained for 60 minutes at 37° C. to permit the GPIIb-IIIa to adsorb onto the walls of the wells. The coating solution is removed by shaking, the wells are rinsed twice with wash buffer (10 mM Tris at pH 7.4, 0.05% (v/v) TWEEN-20, 0.15 M NaCl, and 200 mg/ml merthiolate), and then 200 ul of blocking solution [5% bovine serum albumin (BSA;w/v) in coating solution] are admixed into each well (solid support) to block excess protein sites.

The wells are maintained for 60 minutes at about 37° C. and then the blocking solution is removed. About 50 ul of hybridoma culture supernatant diluted 1:1 in dilution buffer consisting of 0.1% (w/v) BSA in wash buffer is added to each well to form an immunoreaction admixture. The resulting solid/liquid phase immunoreaction admixtures are maintained at room temperature for 60 minutes to permit formation of a first solid phase-bound immunoreaction product between the solid phase-bound polypeptide analog and admixed antibodies. The solid and liquid phases are then separated, the wells are rinsed twice with wash buffer, and excess liquid is removed by shaking.

Fifty ul of a solution containing horseradish peroxidase labeled goat anti-mouse IgG (Tago Inc., Burlingame, Calif.), diluted 1:1000 in dilution buffer is admixed into each well to form a second solid/liquid phase immunoreaction admixture (labeling immunoreaction admixture). The wells are maintained for 60 minutes at room temperature to permit formation of a second immunoreaction product between the labeled antibody and any solid phase-bound antibody of the first immunoreaction product and then rinsed twice with wash buffer to isolate the solid phase-bound label-containing immunoreaction products. Excess liquid is then removed from the wells.

Fifty ul of freshly prepared chromogenic substrate solution containing 4.0 mg/ml 0-phenylenediamine and 0.012% (v/v) hydrogen peroxide in CP buffer (243 ml of 0.1 M citric acid and 250 ml of 0.2 M dibasic sodium phosphate per liter H$_2$O, pH 5.0) are then admixed into each well to form a color developing-reaction admixture. After maintaining the color developing-reaction admixture for 10 minutes at about 20 C, 50 ul of 2 N H$_2$SO$_4$ are admixed into each well to stop the developing-reaction, and the resulting solutions are assayed for absorbance at 490 nanometers (nm) light wavelength using a Model 310 ELISA plate reader (Bio-Tek Instruments, Winooski, Vt.).

Antibody molecule compositions are considered to contain antibody molecules immunoreactive with C-terminal hGPIIb fragment if the measured absorbance at 490 nm (A490) is at least 6 times above background i.e., above about 0.3 optical density units when measured at A490.

b. Competition ELISA Assays to Detect C-Terminal GPIIb Heavy Chain Fragment in Body Fluids Assays to detect C-terminal hGPIIb fragment can be performed on "platelet-poor" plasma, serum or urine samples without concentration. Urine (serum and plasma are used in similar fashion) samples were centrifuged at 15,000×g for 5 min at room temp, and the resulting supernatants were collected to form cell free urine samples. The resulting cell-free urine samples are substantially free of platelets and therefore any hGPIIb fragment present in the sample is in the form of soluble, cell-free, hGPIIb fragment. Fifty microliters (ul) of coating solution (0.1M NaHCO$_3$, pH 8.0, 0.1% NaN$_3$) containing 10 ug/ml of isolated GPIIb-IIIa prepared as described in Example 1b were admixed into the wells of flat-bottom 96-well microtiter plates (Immulon 2; Dynatech Laboratories, Chantilly, Va.). The plates were then maintained for 60 minutes at 37° C. to permit the GPIIb-IIIa to adsorb onto the walls of the wells. The coating solution was removed by shaking and 200 ul of blocking solution [5% bovine serum albumin (BSA;w/v) in coating solution] were admixed into each well (solid support) to block excess protein sites.

The wells were maintained for 60 minutes at about 37° C. and then the blocking solution was removed by rinsing the wells thrice with wash buffer (10 mM Tris at pH 7.4, 0.05% (v/v) TWEEN-20, 0.15 M NaCl, and 200 mg/ml merthiolate). Isolated monoclonal antibody PMI-1 prepared in Example 2c or a control monoclonal antibody (TAB), that immunoreacts with hGPIIb but does not immunoreact with C-terminal hGPIIb fragment, were used in the competition ELISA. TAB was obtained from Dr. R. McEver, University of Texas (San Antonio, Tex.). About 50 ul of monoclonal antibody, diluted 1:1 in incubation buffer consisting of 0.1% (w/v) BSA in wash buffer, was admixed, along with the sample to be tested, to each well to form an immunoreaction admixture. The proportions were as follows:

(a) 20 ul incubation buffer +10 ul of 20 mM EDTA in incubation buffer +20 ul of sample prepared in Example 1c(i); and (b) 50 ul PMI-1 or TAB monoclonal antibody [1:1000 of 4.5 mg/ml IgG (purified on Staph. A columns)].

One set of immunoreaction admixtures was prepared using a test sample, and a second set of immunoreaction admixtures was prepared in which the sample is replaced with a reference standard comprised of a predetermined amount of either isolated GPIIb-IIIa, if the antibody was TAB, or polypeptide V43 (PSPSPIHPAHHKRDRRQ), prepared as in Example 2, if the antibody was PMI-1.

Each immunoreaction admixture was incubated overnight at room temperature to permit formation of a first solid phase-bound immunoreaction product containing the solid phase-bound GPIIb-IIIa and the admixed antibodies.

The solid and liquid phases were then separated, the wells were rinsed thrice with washing buffer, and excess liquid was removed by shaking. Fifty ul of a solution containing horseradish peroxidase labeled goat anti-mouse IgG (Tago Inc., Burlingame, Calif.), diluted 1:1000 in incubation buffer was admixed into each well to form a second solid/liquid phase immunoreaction admixture (labeling immunoreaction admixture). The wells were maintained for 60 minutes at room temperature to permit formation of a second immunoreaction product between the labeled antibody and any solid phase-bound antibody of the first immunoreaction product and then rinsed thrice with wash buffer to isolate the solid phase-bound label-containing immunoreaction products. Excess liquid was then removed from the wells.

Fifty ul of freshly prepared chromogenic substrate solution containing 4.0 mg/ml 0-phenylenediamine and 0.012%

(v/v) hydrogen peroxide in CP buffer (243 ml of 0.1 M citric acid and 250 ml of 0.2 M dibasic sodium phosphate per liter H₂O, pH 5.0) were then admixed into each well to form a color developing-reaction admixture. After maintaining the color developing-reaction admixture for 10 minutes at about 20 C, 50 ul of 2 N H₂SO₄ were admixed into each well to stop the developing-reaction, and the resulting solutions were assayed for absorbance at 490 nanometers (nm) light wavelength using a Model 310 ELISA plate reader (Bio-Tek Instruments, Winooski, Vt.).

Absorbance measurements obtained using standard were plotted against micromolar (uM) concentration of standard in the immunoreaction admixture to produce a standard curve. Absorbance measurements obtained using samples were compared to the standard curve to produce a value expressed as equivalents of standard.

FIGS. 1A and 1B show results of the above competition ELISA using samples containing C-terminal hGPIIb fragment that were formed as described in Example 1c(1). The data is expressed as equivalents of standard (in micromoles) detectable in the sample during the time course of the chymotrypsin digestion. Using polypeptide V43 as a standard in combination with antibody PMI-1, antigenic material that corresponds to C-terminal hGPIIb fragment was released into the supernatant during the course of the digest (FIG. 1A). In contrast, no detectable antigens were released in the supernatant that immunoreact with the TAB antibody (FIG. 1B).

Urine samples from a normal donor in the form of cell free urine samples as described above were tested in the above competition ELISA using various dilutions of urine in incubation buffer from undiluted to 1 part urine to 7 parts buffer (1:8). Equivalents of peptide V43 detectable in the urine using PMI-1 were 1.5 uM at 1:8, 3.8 uM at 1:4 and 1.5 uM at 1:2. From the data, a normalized value of C-terminal hGPIIb fragment in undiluted urine was 14.4 uM for the normal donor's urine. Thus levels of C-terminal hGPIIb fragment in urine that are significantly greater than about 15 uM, such as a 10% increase over normal values, is indicative of thromotic activity above normal levels.

Anti-peptide antibodies prepared as described in Example 3c using the polypeptides shown in Table 1 are used in the competition ELISA in place of monoclonal antibody PMI-1, and using the antibody's corresponding polypeptide rather than isolated GPIIb-IIIa as the solid-phrase antigen. In this assay, samples containing competing antigen, i.e., C-terminal hGPIIb fragment, or containing standard comprised of the same corresponding peptide, are measured as above for the presence and amount of C-terminal hGPIIb fragment. By this competition ELISA assay, anti-peptide antibodies that immunoreact with a polypeptide shown in Table 2 are shown to also immunoreact with isolated GPIIb/IIIa and with C-terminal hGPIIb fragment prepared in Example 1c(2)

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

Sequence Listing

SEQ ID NO 1 illustrates the nucleotide and corresponding amino acid residue sequence of a cDNA that codes for a portion of GPIIb heavy chain (hGPIIb) wherein the nucleotide sequence is shown from left to right and in the direction of 5' terminus to 3' terminus using the single letter nucleotide base code represented as an uninterrupted linear series of bases from base 1 to base 600. The amino acid residue sequence is shown from left to right and in the direction from amino-terminus to carboxy-terminus using the single letter amino acid residue code represented as an uninterrupted linear series of residues from residue 1 (G) at the amino-terminus to residue 200 (K) at the carboxy-terminus.

The reading frame is indicated by the placement of the deduced amino acid residue sequence below the nucleotide sequence such that the single letter that represents each amino acid residue is located below the first base in the corresponding codon.

The nucleotide base sequence shown from base 1 through base 600 in SEQ ID NO 1 corresponds to the nucleotide sequence shown in FIG. 2 of Poncz et al., *J. Biol. Chem.*, 262:8476–8482(1987), from base 2060 to base 2659. The amino acid residue sequence from residue 1 to residue 200 shown in SEQ ID NO 1 corresponds to the sequence shown in FIG. 2 of Poncz et al., supra, from residue 656 to residue 855.

SEQ ID NO 1:

```
GGCGCCCACTACATGCGGGCCCTAAGCAATGTCGAGGGCTTTGAGAGACTCATCTGTAAT    60
G   A   H   Y   M   R   A   L   S   N   V   E   G   F   E   R   L   I   C   N       20

CAGAAGAAGGAGAATGAGACCAGGGTGGTGCTGTGTGAGCTGGGCAACCCCATGAAGAAG   120
Q   K   K   E   N   E   T   R   V   V   L   C   E   L   G   N   P   M   K   K       40

AACGCCCAGATAGGAATCGCGATGTTGGTGAGCGTGGGGAATCTGGAAGAGGCTGGGGAG   180
N   A   Q   I   G   I   A   M   L   V   S   V   G   N   L   E   E   A   G   E       60

TCTGTGTCCTTCCAGCTGCAGATACGGAGCAAGAACAGCCAGAATCCAAACAGCAAGATT   240
S   V   S   F   Q   L   Q   I   R   S   K   N   S   Q   N   P   N   S   K   I       80

GTGCTGCTGGACGTGCCGGTCCGGGCAGAGGCCCAAGTGGAGCTGCGAGGGAACTCCTTT   300
V   L   L   D   V   P   V   R   A   E   A   Q   V   E   L   R   G   N   S   F      100

CCAGCCTCCCTGGTGGTGGCAGCAGAAGAAGGTGAGAGGGAGCAGAACAGCTTGGACAGC   360
P   A   S   L   V   V   A   A   E   E   G   E   R   E   Q   N   S   L   D   S      120
```

-continued

```
TGGGGACCCAAAGTGGAGCACACCTATGAGCTCCACAACACTGGCCCTGGGACTGTGAAT    420
 W   G   P   K   V   E   H   T   Y   E   L   H   N   T   G   P   G   T   V   N       140

GGTCTTCACCTCAGCATCCACCTTCCGGGACAGTCCCAGCCCTCCGACCTGCTCTACATC    480
 G   L   H   L   S   I   H   L   P   G   Q   S   Q   P   S   D   L   L   Y   I       160

CTTGGATATACAGCCCCAGGGGCGCTTCAGTGCTTCCCACAGCCTCCTGTCAATCCTCTC    540
 L   D   I   Q   P   Q   G   A   L   Q   C   F   P   Q   P   P   V   N   P   L       180

AAGGTGGACTGGGGGCTGCCCATCCCCAGCCCCTCCCCCATTCACCCGGCCCATCACAAG    600
 K   V   D   W   G   L   P   I   P   S   P   S   P   I   H   P   A   H   H   K       200
```

---

What is claimed is:

1. An antibody composition comprising an antibody that immunoreacts with amino acid residue sequence as shown in SEQ ID NO 1 from residue 173 to residue 193, and does not specifically bind with amino acid residue sequence REQNSLDSWGPK (SEQ ID NO 1 from residue 113 to residue 124).

2. The composition of claim 1 wherein said antibody is a monoclonal antibody.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 600 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..600
      (D) OTHER INFORMATION: /standard_name= "Portion of GPIIb
         heavy chain"

(xi) SEQUENCE DESCRIPTION: SEQ ID NO:1:

```
GGC GCC CAC TAC ATG CGG GCC CTA AGC AAT GTC GAG GGC TTT GAG AGA        48
Gly Ala His Tyr Met Arg Ala Leu Ser Asn Val Glu Gly Phe Glu Arg
 1               5                  10                  15

CTC ATC TGT AAT CAG AAG AAG GAG AAT GAG ACC AGG GTG GTG CTG TGT        96
Leu Ile Cys Asn Gln Lys Lys Glu Asn Glu Thr Arg Val Val Leu Cys
             20                  25                  30

GAG CTG GGC AAC CCC ATG AAG AAG AAC GCC CAG ATA GGA ATC GCG ATG       144
Glu Leu Gly Asn Pro Met Lys Lys Asn Ala Gln Ile Gly Ile Ala Met
         35                  40                  45

TTG GTG AGC GTG GGG AAT CTG GAA GAG GCT GGG GAG TCT GTG TCC TTC       192
Leu Val Ser Val Gly Asn Leu Glu Glu Ala Gly Glu Ser Val Ser Phe
     50                  55                  60

CAG CTG CAG ATA CGG AGC AAG AAC AGC CAG AAT CCA AAC AGC AAG ATT       240
Gln Leu Gln Ile Arg Ser Lys Asn Ser Gln Asn Pro Asn Ser Lys Ile
 65                  70                  75                  80

GTG CTG CTG GAC GTG CCG GTC CGG GCA GAG GCC CAA GTG GAG CTG CGA       288
Val Leu Leu Asp Val Pro Val Arg Ala Glu Ala Gln Val Glu Leu Arg
                 85                  90                  95

GGG AAC TCC TTT CCA GCC TCC CTG GTG GTG GCA GCA GAA GAA GGT GAG       336
Gly Asn Ser Phe Pro Ala Ser Leu Val Val Ala Ala Glu Glu Gly Glu
            100                 105                 110

AGG GAG CAG AAC AGC TTG GAC AGC TGG GGA CCC AAA GTG GAG CAC ACC       384
Arg Glu Gln Asn Ser Leu Asp Ser Trp Gly Pro Lys Val Glu His Thr
        115                 120                 125

TAT GAG CTC CAC AAC ACT GGC CCT GGG ACT GTG AAT GGT CTT CAC CTC       432
```

```
                Tyr Glu Leu His Asn Thr Gly Pro Gly Thr Val Asn Gly Leu His Leu
                    130                 135                 140

AGC ATC CAC CTT CCG GGA CAG TCC CAG CCC TCC GAC CTG CTC TAC ATC                 480
Ser Ile His Leu Pro Gly Gln Ser Gln Pro Ser Asp Leu Leu Tyr Ile
145                 150                 155                 160

CTG GAT ATA CAG CCC CAG GGG GCG CTT CAG TGC TTC CCA CAG CCT CCT                 528
Leu Asp Ile Gln Pro Gln Gly Ala Leu Gln Cys Phe Pro Gln Pro Pro
                165                 170                 175

GTC AAT CCT CTC AAG GTG GAC TGG GGG CTG CCC ATC CCC AGC CCC TCC                 576
Val Asn Pro Leu Lys Val Asp Trp Gly Leu Pro Ile Pro Ser Pro Ser
        180                 185                 190

CCC ATT CAC CCG GCC CAT CAC AAG                                                  600
Pro Ile His Pro Ala His His Lys
    195                 200

(2) INFORMATION FOR SEQ ID NO:2:

(i) SEQUENCE CHARACTERISTICS:
          (A) LENGTH: 17 amino acids
          (B) TYPE: amino acid
          (D) TOPOLOGY: unknown (ii) MOLECULE TYPE: peptide (v) FRAGMENT TYPE: internal (xi) SEQUENCE DESCRIPTION: SEQ ID NO:2:

Pro Ser Pro Ser Pro Ile His Pro Ala His His Lys Arg Asp Arg Arg
1               5                   10                  15

Gln (2) INFORMATION FOR SEQ ID NO:3:

(i) SEQUENCE CHARACTERISTICS:
          (A) LENGTH: 200 amino acids
          (B) TYPE: amino acid
          (D) TOPOLOGY: linear (ii) MOLECULE TYPE: protein (xi) SEQUENCE DESCRIPTION: SEQ ID NO:3:

Gly Ala His Tyr Met Arg Ala Leu Ser Asn Val Glu Gly Phe Glu Arg
1               5                   10                  15

Leu Ile Cys Asn Gln Lys Lys Glu Asn Glu Thr Arg Val Val Leu Cys
                20                  25                  30

Glu Leu Gly Asn Pro Met Lys Lys Asn Ala Gln Ile Gly Ile Ala Met
            35                  40                  45

Leu Val Ser Val Gly Asn Leu Glu Glu Ala Gly Glu Ser Val Ser Phe
        50                  55                  60

Gln Leu Gln Ile Arg Ser Lys Asn Ser Gln Asn Pro Asn Ser Lys Ile
65                  70                  75                  80

Val Leu Leu Asp Val Pro Val Arg Ala Glu Ala Gln Val Glu Leu Arg
                85                  90                  95

Gly Asn Ser Phe Pro Ala Ser Leu Val Val Ala Ala Glu Glu Gly Glu
            100                 105                 110

Arg Glu Gln Asn Ser Leu Asp Ser Trp Gly Pro Lys Val Glu His Thr
        115                 120                 125

Tyr Glu Leu His Asn Thr Gly Pro Gly Thr Val Asn Gly Leu His Leu
    130                 135                 140

Ser Ile His Leu Pro Gly Gln Ser Gln Pro Ser Asp Leu Leu Tyr Ile
145                 150                 155                 160
```

```
Leu Asp Ile Gln Pro Gln Gly Ala Leu Gln Cys Phe Pro Gln Pro Pro
                165                 170                 175

Val Asn Pro Leu Lys Val Asp Trp Gly Leu Pro Ile Pro Ser Pro Ser
            180                 185                 190

Pro Ile His Pro Ala His His Lys
        195             200
```